(12) United States Patent
Yi et al.

(10) Patent No.: US 9,506,848 B2
(45) Date of Patent: Nov. 29, 2016

(54) FREQUENCY DOUBLING ANTENNA SENSOR FOR WIRELESS STRAIN AND CRACK SENSING

(71) Applicants: Xiaohua Yi, Atlanta, GA (US);
Chunhee Cho, Atlanta, GA (US);
Benjamin Cook, Atlanta, GA (US);
Yang Wang, Atlanta, GA (US); Manos Tentzeris, Atlanta, GA (US); Roberto T. Leon, Atlanta, GA (US)

(72) Inventors: Xiaohua Yi, Atlanta, GA (US);
Chunhee Cho, Atlanta, GA (US);
Benjamin Cook, Atlanta, GA (US);
Yang Wang, Atlanta, GA (US); Manos Tentzeris, Atlanta, GA (US); Roberto T. Leon, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 148 days.

(21) Appl. No.: 14/459,219

(22) Filed: Aug. 13, 2014

(65) Prior Publication Data

US 2015/0047436 A1 Feb. 19, 2015

Related U.S. Application Data

(60) Provisional application No. 61/865,371, filed on Aug. 13, 2013.

(51) Int. Cl.
*G01L 1/00* (2006.01)
*G01N 3/02* (2006.01)
*G01M 5/00* (2006.01)

(52) U.S. Cl.
CPC .............. *G01N 3/02* (2013.01); *G01M 5/0033* (2013.01); *G01M 5/0083* (2013.01)

(58) Field of Classification Search
CPC .................... G01N 27/025; G01N 2203/0617; G01N 35/00871; G01N 2203/0062; G01M 5/0083; G01M 5/0033; A61B 5/686; A61B 5/0004; A61B 2562/0261; A61B 5/002; A61B 5/0031; A61B 17/7002; A61B 5/1116; A61B 2017/0021; A61B 5/076; A61B 5/4504; A61B 2560/0223; A61B 2560/0219; A61B 5/1038; A61B 5/7225; A61B 5/0024; A61B 2562/12; A61B 5/7228; A61B 5/6807; A61B 2562/04; A61B 2562/0252; G01B 7/24; G01B 7/16; G01B 15/06; H01Q 1/2225; H01Q 21/065; H01Q 7/00; G01F 15/066; G01F 25/00; G01L 9/0073; G01L 1/14; G01L 1/00; G01L 19/086; G01L 5/0038; G08B 1/08; G01R 31/2858; G01R 31/2896; G01R 31/2601; G01R 31/2856; H01L 22/34; H01L 23/585; H01L 2924/0002; H01L 2924/00; H01L 21/78
USPC ......... 73/774, 755, 773, 763, 775–776, 633, 73/655, 799; 702/34; 324/655, 763, 633
See application file for complete search history.

(56) References Cited

U.S. PATENT DOCUMENTS 6,973,838 B2    12/2005  Denis
(Continued)

OTHER PUBLICATIONS

Deivasigamani et al: "A Review of Passive Wireless Sensors for Structural Health Monitoring", Jan. 29, 2013; pp. 57-76; Modern Applied Science; vol. 7, No. 2.
(Continued)

*Primary Examiner* — Harshad R Patel
*Assistant Examiner* — Brandi Hopkins
(74) *Attorney, Agent, or Firm* — Bryan W. Bockhop; Bockhop Intellectual Property Law, LLC

(57) ABSTRACT

A strain and crack sensor senses an amount of strain induced in an object. A receiving planar antenna has a first resonant frequency and is configured to receive a querying signal at the first resonant frequency. A transmitting planar antenna has a second resonant frequency that is twice the first resonant frequency. At least one of the receiving planar antenna and the transmitting planar antenna is bonded to the object so that at least one of strain induced in the object or a crack formed in the object causes a shift in at least one of the first resonant frequency or the second resonant frequency. A matching element is in electrical communication with the first planar antenna and the second planar antenna. The matching element is configured to cause the transmitting planar antenna to radiate a response signal in response to the querying signal.

18 Claims, 3 Drawing Sheets

(56) References Cited

U.S. PATENT DOCUMENTS

| | | | |
|---|---|---|---|
| 7,038,455 B2* | 5/2006 | Beste | G01V 3/28 |
| | | | 324/333 |
| 7,849,752 B2 | 12/2010 | Gregory et al. | |
| 7,975,554 B2 | 7/2011 | Berkcan et al. | |
| 8,104,358 B1 | 1/2012 | Jia et al. | |
| 2006/0214842 A1* | 9/2006 | Takenoshita | G01S 7/03 |
| | | | 342/175 |
| 2011/0040498 A1* | 2/2011 | Huang | G01B 7/16 |
| | | | 702/34 |
| 2011/0152725 A1 | 6/2011 | Demir et al. | |
| 2012/0109560 A1 | 5/2012 | Huang et al. | |
| 2012/0286935 A1 | 11/2012 | Huang | |
| 2012/0297888 A1 | 11/2012 | Nagarajan et al. | |
| 2013/0099789 A1 | 4/2013 | Benslimane et al. | |
| 2013/0176036 A1* | 7/2013 | Grozinger | G01R 27/2611 |
| | | | 324/655 |
| 2014/0056368 A1* | 2/2014 | Nakayama | H01Q 21/28 |
| | | | 375/256 |
| 2014/0302797 A1* | 10/2014 | Han | H04W 24/06 |
| | | | 455/67.14 |
| 2015/0372383 A1* | 12/2015 | Yoshida | H01Q 1/2291 |
| | | | 343/853 |

OTHER PUBLICATIONS

Mohammad et al: "An Antenna Sensor for Crack Detection and Monitoring"; Feb. 15, 2011, p. 47; Multi Science Publishing; vol. 14, No. 1.

Ahbe et al: "Dual-Band Antennas for Frequency-Doubler-Based Wireless Strain Sensing"; Feb. 14, 2012; Antennas and Wireless Propagation Letters, IEEE (Abstract).

Melik et al: "Flexible metamaterials for wireless strain sensing"; Nov. 4, 2009; pp. 95-97; Applied Physics Letters; 95.

Daliri et al: "Slotted Circular Microstrip Patch Antenna Application in Strain Based Structural Health Monitoring"; 2011; 7th DSTO International Conference on Health & Usage Monitoring (HUMS 2011)—AIAC14 Fourteenth Australian International Aerospace Congress.

* cited by examiner

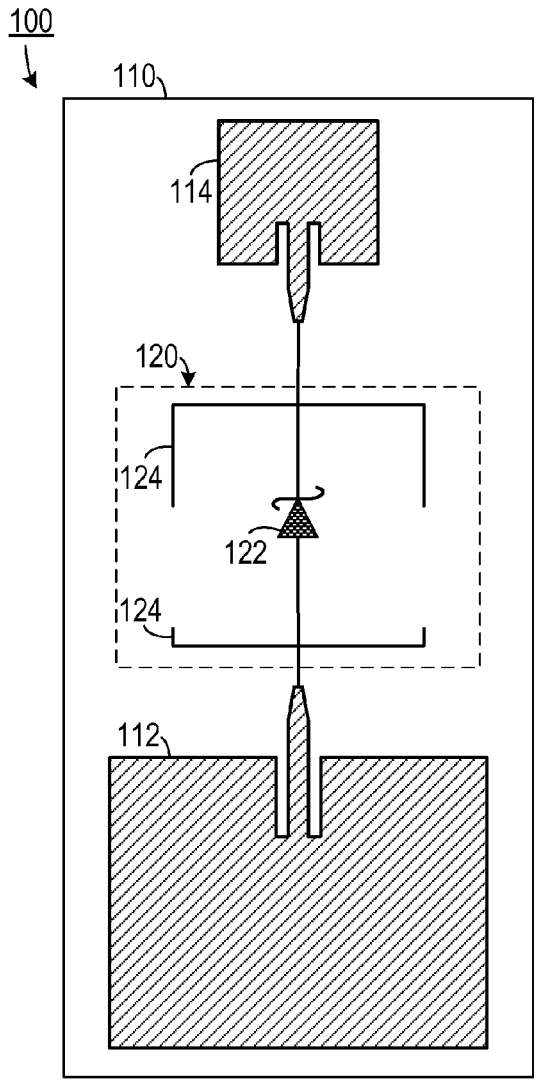
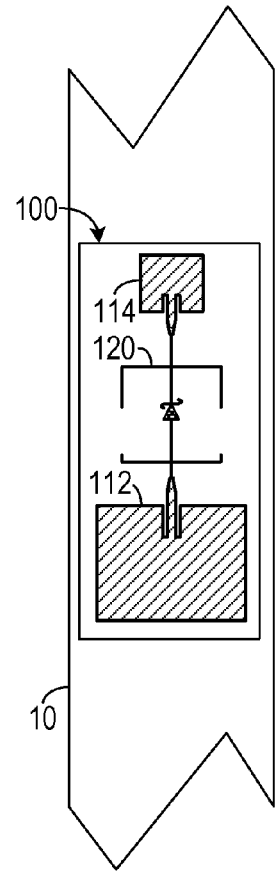
FIG. 1
FIG. 2
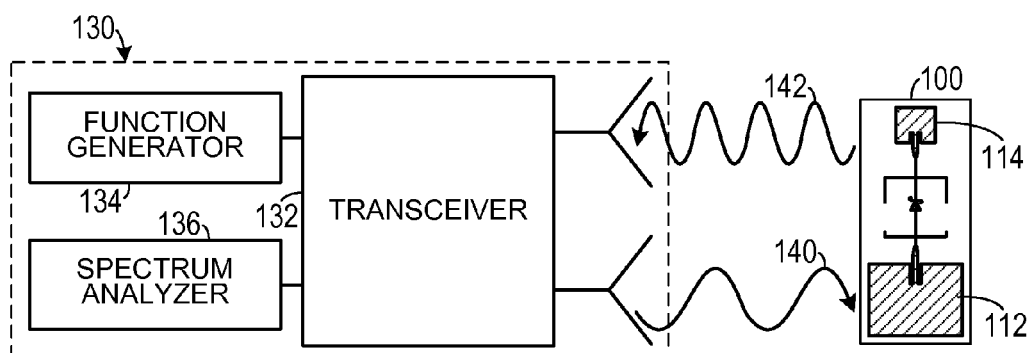
FIG. 3

FREQUENCY DOUBLING ANTENNA SENSOR FOR WIRELESS STRAIN AND CRACK SENSING

CROSS-REFERENCE TO RELATED APPLICATION(S)

This application claims the benefit of U.S. Provisional Patent Application Ser. No. 61/865,371, filed Aug. 13, 2013, the entirety of which is hereby incorporated herein by reference.

STATEMENT OF GOVERNMENT INTEREST

This invention was made with government support under agreement No. DTFH61-10-H-00004, awarded by the DOT, Federal Highway Administration. The government has certain rights in the invention.

BACKGROUND OF THE INVENTION

1. Field of the Invention

The present invention relates to strain and crack sensors and, more specifically, to a wireless passive strain and crack sensing systems.

2. Description of the Related Art

In order to accurately assess deterioration of civil, mechanical, and aerospace structures, there has been a large volume of research in structural health monitoring (SHM) over past few decades. Sensors can be used to measure various structural responses and operating conditions, including: strain, displacement, acceleration, humidity, temperature, etc. Among these measurements, strain can be an important indicator for stress concentration and damage development.

Metal foil strain gages are currently among the most common solutions due to their low-cost, simple circuitry, and acceptable reliability in many applications. However, when applied to large structures, traditional metal foil strain gages require lengthy cable connections for power and data acquisition, which can significantly increase installation time and system cost.

Wireless strain sensors have recently been developed to avoid cabling difficulty associated with metal foil strain gages. For example, one wireless strain sensor employs the inductive coupling principle involving two adjacent inductors. However, the interrogation distance achieved by inductive coupling is usually limited to several inches, which is inconvenient for many practical applications. Electromagnetic backscattering techniques have been exploited for wireless strain sensing in an attempt to increase interrogation distance.

Since the electromagnetic resonance frequency of a planar antenna is related to the antenna's physical dimension, the resonance frequency changes when the antenna is under strain. This relationship between resonance frequency and strain can be used for stress/strain measurement of a structure to which the planar antenna is bonded. For example, a patch antenna has been designed for wireless strain sensing in which a phototransistor is adapted for signal modulation of the RF signal backscattered from the antenna sensor. As a result, signal backscattered from the sensor can be distinguished from environmental reflections. However, the light-switching mechanism is not practical for outdoor application, where light intensity is usually so strong that the phototransistor is constantly activated and thus, loses the ability to switch.

To avoid this difficulty, a low-cost off-the-shelf radiofrequency identification (RFID) chip has been previously adopted as a simple mechanism for signal modulation. Since the RFID chip is powered by a wireless interrogation signal, the RFID-based strain sensor is wireless and passive (i.e., battery-free). One prototype RFID antenna sensor has shown a strain measurement resolution of 20µ∈ in laboratory experiments, and can measure large strains up to 10,000µ∈. Previous studies demonstrated that if operating frequency of the wireless strain sensor is increased, strain sensitivity can be improved and sensor size can be reduced. However, the RFID chip only functions in the frequency band of 860-960 MHz.

Therefore, there is a need for a wireless passive strain sensor that is configured to operate at frequencies higher than typical RFID frequencies.

SUMMARY OF THE INVENTION

The disadvantages of the prior art are overcome by the present invention which, in one aspect, is a strain and crack sensor for sensing an amount of strain induced in an object. A receiving planar antenna has a first resonant frequency and is configured to receive a querying signal at the first resonant frequency. A transmitting planar antenna has a second resonant frequency that is twice the first resonant frequency. At least one (or both) of the receiving planar antenna and the transmitting planar antenna is bonded to the object so that at least one of strain induced in the object or a crack formed in the object causes a shift in at least one (or both) of the first resonant frequency or the second resonant frequency. A matching element is in electrical communication with the first planar antenna and the second planar antenna. The matching element is configured to cause the transmitting planar antenna to radiate a response signal in response to the querying signal.

In another aspect, the invention is a sensing system for sensing an strain and a crack in an object. A receiving planar antenna has a first resonant frequency and is configured to receive a querying signal at the first resonant frequency. A transmitting planar antenna has a second resonant frequency that is twice the first resonant frequency. At least one (or both) of the receiving planar antenna and the transmitting planar antenna is bonded to the object so that at least one of strain induced in the object or a crack formed in the object causes a shift in at least one (or both) of the first resonant frequency or the second resonant frequency. A matching element is in electrical communication with the receiving planar antenna and the transmitting planar antenna. The matching element is configured to cause the transmitting planar antenna to radiate a response signal in response to the querying signal. The matching element includes a Schottky diode having a cathode side that is in electrical communication with the transmitting planar antenna and an anode side that is in electrical communication with the receiving planar antenna. A sensing unit that includes a transceiver that is configured to radiate the querying signal and to receive the response signal; a spectrum analyzing circuit configured to detect the response signal frequency; and a processor configured to calculate the amount of strain induced in an object.

In yet another aspect, the invention is a method of sensing stain and a crack in an object, in which a querying signal having a first frequency is transmitted to a receiving planar antenna that has a first resonant frequency. A response signal is received from a transmitting planar antenna that has a second resonant frequency that is twice the first resonant frequency. At least one of the receiving planar antenna and the transmitting planar antenna is bonded to the object so that at least one of strain in the object or the crack in the object will cause a frequency shift in the response signal. An amount of frequency shift between the response signal frequency and twice the querying signal frequency is detected. An amount of strain or the presence of a crack is determined based on the amount of frequency shift.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIG. 1 is a schematic view of a first embodiment of a sensing element.

FIG. 2 is a schematic view of a sensing element applied to an object.

FIG. 3 is a schematic view of a sensing system.

DETAILED DESCRIPTION OF THE INVENTION

Figure 4:
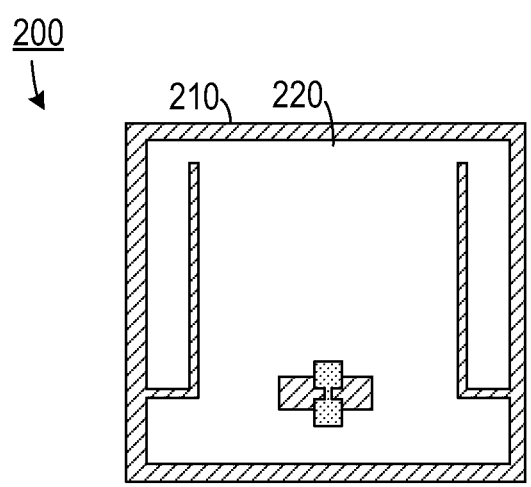
FIG. 4 is a schematic view of a second embodiment of a sensing antenna.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIGS. 1-3, one embodiment of a strain and crack sensor 100 includes a thin dielectric substrate 110, a receiving patch antenna 112 having a first resonant frequency disposed on the substrate, a transmitting patch antenna 114 also disposed on the substrate and having a second resonant frequency that is twice the first resonant frequency. A matching network 120 electrically couples the receiving patch antenna 112 to the transmitting patch antenna 114. In one embodiment, the matching network 120 includes a GaAs Schottky diode 122, which ensures that current flowing from the receiving patch antenna 112 is delivered to the transmitting patch antenna 114 with a doubled frequency. The matching network 120 also includes a pair of electromagnetic matching lines 124.

Figure 5:
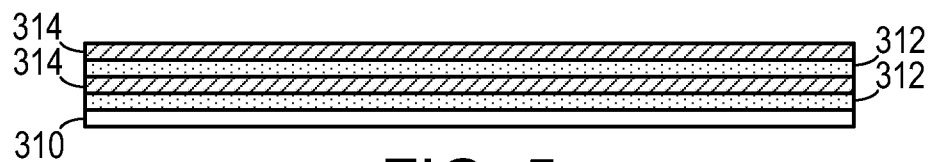
FIG. 5 is a side schematic view of one embodiment of an antenna.

In other embodiments, as shown in FIG. 5, the receiving antenna 112 and the transmitting antenna 114 can include a plurality of dielectric layers 312 disposed on the ground plane 310 and a plurality of conductive radiating layers 314 that are interleaved with the plurality of dielectric layers 312. Also, in other embodiments, the receiving planar antenna 112 and the transmitting planar antenna 114 can include patch antennas, wideband antennas, frequency selection surface (FSS) antennas, and combinations thereof.

When at least one of the receiving patch antenna 112 or the transmitting patch antenna 114 is firmly affixed to an object 10 (such as a steel beam used in a bridge), any strain induced in the object 10, or any cracks forming therein, will cause the affixed antenna to distort, thereby causing a resonant frequency shift in the antenna.

When a sensing unit 130, which includes a radio frequency transceiver 132, transmits a querying signal 140 (generated by a function generator 134) at a frequency corresponding to the first resonant frequency to the sensor 100, the receiving patch antenna 112 will harvest energy from the querying signal and resonate therein. This causes a current at resonant frequency of the receiving patch antenna 112 to flow to the transmitting patch antenna 114 through the Schottky diode 122, which results in a doubling of the frequency of the current flowing into the transmitting patch antenna 114. As a result, a response signal 142 is radiated from the transmitting patch antenna 114. Any distortion experienced by the receiving patch antenna 112 or the transmitting patch antenna 114 will cause a resonant frequency shift in the respective antenna, which will cause the response signal 142 to be radiated with a frequency with a corresponding shift. The frequency of the response signal 142 is detected by spectrum analyzing circuitry 136 and a processor associated with the spectrum analyzer 136 can measure the frequency shift in the response signal 142 and correlate the shift with the amount of strain or the presence of a crack in the object 10.

The system 100 uses energy harvested from the querying signal 140 to generate the response signal 142 and, therefore, does not require a separate power source. Because the response signal 142 has a frequency that is nominally double the frequency of the querying signal 140, the sensing unit 130 can easily distinguish between the response signal 142 and any local reflections of the querying signal 140.

Another example embodiment of the transmitting planar antenna, or the receiving planar antenna, as shown in FIG. 4, employs a slotted patch antenna 200 that includes a conductive element 220 disposed on a substrate 210. Instead of being a simple patch antenna, slot patterns are introduced on the conductive element so that the overall antenna dimension is reduced. Other embodiments that may be employed include: folded patch antennas, wideband antennas, and frequency selection surface (FSS) antennas.

One experimental embodiment of a strain sensor design employed a frequency doubling scheme to enable sensor operation at a high frequency. The basic concept was to let the sensor double the frequency of reader interrogation signal ($f$) and backscatter signal at the doubled frequency ($2f$). Because environmental reflections to reader interrogation signal are concentrated at $f$, the reader only receives signal at $2f$ backscattered from the sensor. The frequency doubling operation was implemented through a Schottky diode, which is a nonlinear circuit device that can generate an output signal with frequencies at multiples of input frequency. The GaAs Schottky diode used provided a 1% conversion efficiency at −30 dBm input power.

In this experimental embodiment, the diode-enabled frequency doubling mechanism was incorporated with two patch antennas to form a wireless strain sensor. A Schottky diode (SMS7621-079LF) from Skyworks Solutions, Inc. was used in the matching network. A patch antenna with resonance frequency at 2.9 GHz was used as a receiving antenna of the wireless strain sensor. Meanwhile, another patch antenna with resonance frequency at 5.8 GHz was used to serve as a transmitting antenna of the wireless strain sensor. The three components, i.e. the receiving and transmitting antennas and matching network, were combined together to form a frequency doubling antenna sensor. Since operation power of the diode is harvested from wireless interrogation signal, the frequency doubling antenna sensor is wireless and passive (battery-free). Strain sensing simulation shows that the proposed frequency doubling sensor can achieve a strain sensitivity of −3.84 kHz/µ∈.

In the experimental embodiment, the sensor included three main components: a receiving antenna (with resonance frequency $f_0$), a transmitting antenna (with resonance frequency $2f_0$), and a diode-integrated matching network between receiving and transmitting antennas. During operation, a wireless interrogation signal is emitted from the reader side by a function generator and through a transmitting reader antenna. If interrogation frequency $f$ is in the neighborhood of $f_0$, resonance frequency of the receiving patch antenna at sensor side, interrogation power is captured by the sensor-side receiving patch antenna and transferred to the matching network. The diode then generates output signal at doubled frequency $2f$. The output signal at $2f$ is backscattered to reader through sensor-side transmitting patch antenna (resonance frequency at $2f_0$). A spectrum analyzer finally measures the backscattered signal at reader side. Frequency of backscattered sensor signal is at $2f$, and the unwanted environmental reflections to original reader interrogation signal remains at $f$. Therefore, it is easy for the spectrum analyzer to distinguish backscattered sensor signal from unwanted environmental reflections.

In this experimental embodiment, the receiving and transmitting antennas of the frequency doubling sensor were microstrip patch antennas. For a microstrip patch antenna with length L, width W, and substrate thickness h, effective dielectric constant of the antenna can be calculated for determining antenna electrical length:

$$\varepsilon_{\mathit{reff}} = \frac{\varepsilon_r+1}{2} + \frac{\varepsilon_r-1}{2}\left[1+12\frac{h}{w}\right]^{-\frac{1}{2}} \quad (1)$$

where $\in_r$ is the substrate dielectric constant. The resonance frequency ($f_0$) of a patch antenna at zero strain level can be estimated as:

$$f_0 = \frac{c}{2(L+2\Delta L)\sqrt{\varepsilon_{\mathit{reff}}}} \quad (2)$$

where c is the speed of light; ΔL is antenna length compensation due to fringing effect, which was determined empirically by:

$$\Delta L = 0.412\frac{(\varepsilon_{\mathit{reff}}+0.3)\left(\frac{W}{h}+0.264\right)h}{(\varepsilon_{\mathit{reff}}-0.258)\left(\frac{W}{h}+0.8\right)} \quad (3)$$

By defining coefficient k as:

$$k = 0.412\frac{(\varepsilon_{\mathit{reff}}+0.3)\left(\frac{W}{h}+0.264\right)}{(\varepsilon_{\mathit{reff}}-0.258)\left(\frac{W}{h}+0.8\right)} \quad (4)$$

ΔL can be rewritten as:

$$\Delta L = kh \quad (5)$$

When the patch antenna is under strain ∈ along the direction of patch length L, physical dimensions of the patch antenna are changed accordingly. This change causes shift in resonance frequency:

$$f = \frac{c}{2[L(1+\varepsilon)+2kh(1-v\varepsilon)]\sqrt{\varepsilon_{\mathit{reff}}}} \quad (6)$$

$$= \frac{c}{2[(L+2kh)+(L-v2khv)\varepsilon]\sqrt{\varepsilon_{\mathit{reff}}}}$$

$$\approx f_0\left(1-\frac{L-2khv}{L+2kh}\varepsilon\right)$$

$$= f_0 - S\varepsilon$$

where v is Poisson's ratio of substrate material; represents strain sensitivity of the patch antenna. According to Eq. (6), when strain is small, resonance frequency change of the patch antenna has an approximately linear relationship with applied strain. This serves as strain sensing mechanism of the patch antenna. In this paper, it is assumed that only receiving antenna of a frequency doubling sensor is bonded to structural surface, while matching network and transmitting antenna are floating and stress/strain free. Through the matching network and transmitting patch antenna, this frequency shift causes change in the backscattered signal, which is captured by the reader. This change in the backscattered signal is used to derive strain on the monitored structure.

In the experimental embodiment, the substrate material used in was Rogers/Duroid® 5880, a glass micro-fiber reinforced PTFE material. A 31 mil substrate thickness was chosen, which represents a trade-off between increasing wireless interrogation distance and improving strain transfer ratio from structural surface to top layer of the microstrip patch antenna. The dielectric constant $\in_r$ of the material was 2.2. The resonance frequency was set $f_0$=2.9 GHz for the receiving antenna, and $2f_0$=5.8 GHz for the transmitting antenna.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A strain and crack sensor for sensing an amount of stress concentration induced in an object, comprising:
   (a) a dielectric substrate bonded to the object;
   (b) a receiving planar antenna disposed on the dielectric substrate and having a first resonant frequency, the receiving planar antenna configured to receive a querying signal at the first resonant frequency;
   (c) a transmitting planar antenna disposed on the dielectric substrate and having a second resonant frequency that is twice the first resonant frequency, at least one of the receiving planar antenna and the transmitting planar antenna being bonded to the dielectric substrate so that strain induced in the object or a crack formed in the object causes a shift in at least one of the first resonant frequency or the second resonant frequency; and
   (d) a matching network, disposed on the dielectric substrate, in electrical communication with the first planar antenna and the second planar antenna, the matching network configured to transfer current from the receiving planar antenna to the transmitting planar antenna at the second resonant frequency when the receiving planar antenna receives the querying signal, thereby causing the transmitting planar antenna to radiate a response signal in response to the querying signal at the second resonant frequency.

2. The strain and crack sensor of claim 1, wherein the receiving planar antenna has a greater surface area that the transmitting planar antenna.

3. The strain and crack sensor of claim 2, wherein the receiving planar antenna and the transmitting planar antenna comprise:
   (a) a conductive ground plane;
   (b) a dielectric layer disposed on the ground plane; and
   (c) a conductive radiating layer disposed on the dielectric layer.

4. The strain and crack sensor of claim 2, wherein the receiving planar antenna and the transmitting planar antenna comprise:
   (a) a plurality of dielectric layers disposed on the ground plane; and
   (b) a plurality of conductive radiating layers interleaved with the plurality of dielectric layers.

5. The strain and crack sensor of claim 1, wherein the receiving planar antenna and the transmitting planar each comprise an antenna selected from a group of antennas consisting of: patch antennas; wideband antennas frequency selection surface (FSS) antennas, and combinations thereof.

6. The strain and crack sensor of claim 1, wherein the matching network comprises:
   (a) a Schottky diode; and
   (b) electromagnetic matching lines.

7. The strain and crack sensor of claim 6, wherein the Schottky diode has a cathode side and an anode side, wherein the cathode side is in electrical communication with the transmitting planar antenna and wherein the anode side is in electrical communication with the receiving planar antenna.

8. The strain and crack sensor of claim 7, wherein the Schottky diode comprises a GaAs Schottky diode.

9. The strain and crack sensor of claim 1, further comprising:
   (a) a transceiver that is configured to radiate the querying signal and to receive the response signal;
   (b) a spectrum analyzing circuit configured to detect the response signal frequency; and
   (c) a processor configured to calculate the amount of strain induced in an object.

10. A sensing system for sensing a strain and a crack in an object, comprising:
    (a) a dielectric substrate bonded to the object;
    (b) a receiving planar antenna disposed on the dielectric substrate and having a first resonant frequency, the receiving planar antenna configured to receive a querying signal at the first resonant frequency;
    (c) a transmitting planar antenna disposed on the dielectric substrate and having a second resonant frequency that is twice the first resonant frequency, at least one of the receiving planar antenna and the transmitting planar antenna being bonded to the dielectric substrate so that strain induced in the object or a crack formed in the object causes a shift in at least one of the first resonant frequency or the second resonant frequency;
    (d) a matching network, disposed on the dielectric substrate, in electrical communication with the receiving planar antenna and the transmitting planar antenna, the matching network configured to transfer current from the receiving planar antenna to the transmitting planar antenna at the second resonant frequency when the receiving planar antenna receives the querying signal, thereby causing the transmitting planar antenna to radiate a response signal in response to the querying signal at the second resonant frequency, the matching network including a Schottky diode having a cathode side that is in electrical communication with the transmitting planar antenna and an anode side that is in electrical communication with the receiving planar antenna, the matching network also including electromagnetic matching lines; and
    (e) a sensing unit, that includes:
      (i) a transceiver that is configured to radiate the querying signal and to receive the response signal;
      (ii) a spectrum analyzing circuit configured to detect the response signal frequency; and
      (iii) a processor configured to calculate the amount of strain induced in an object.

11. The sensing system of claim 10, wherein the receiving planar antenna comprises a first patch antenna and wherein the transmitting planar antenna comprises a second patch antenna, the first patch antenna having a greater surface area that the second patch antenna.

12. The sensing system of claim 10, wherein the receiving planar antenna and the transmitting planar each comprise an antenna selected from a group of antennas consisting of: patch antennas; wideband antennas frequency selection surface (FSS) antennas, and combinations thereof.

13. The sensing system of claim 10, wherein the Schottky diode comprises a GaAs Schottky diode.

14. A method of sensing stain and a crack in an object, comprising the steps of:
    (a) transmitting a querying signal having a first frequency to a receiving planar antenna that has a first resonant frequency;
    (b) receiving a response signal having a second frequency different from the first frequency from a transmitting planar antenna that has a second resonant frequency that is twice the first resonant frequency, where at least one of the receiving planar antenna and the transmitting planar antenna is bonded to the object so that at least one of strain in the object or the crack in the object will cause a frequency shift in the response signal;
    (c) detecting an amount of frequency shift between the response signal frequency and twice the querying signal frequency; and
    (d) determining an amount of strain or the presence of a crack based on the amount of frequency shift.

15. The method of claim 14, wherein the receiving planar antenna comprises a first patch antenna and wherein the transmitting planar antenna comprises a second patch antenna, the first patch antenna having a greater surface area that the second patch antenna.

16. The method of claim 14, further comprising the step of matching the transmitting planar antenna with the receiving planar antenna with a matching network, wherein the matching network comprises:
    (a) a Schottky diode; and
    (b) electromagnetic matching lines.

17. The method of claim 16, wherein the Schottky diode has a cathode side and an anode side, an further comprising the steps of electrically coupling the cathode side to the transmitting planar antenna and electrically coupling the anode side to the receiving planar antenna.

18. The method of claim 17, wherein the Schottky diode comprises a GaAs Schottky diode.

* * * * *